US012678398B2

(12) United States Patent
Chung et al.

(10) Patent No.: US 12,678,398 B2
(45) Date of Patent: Jul. 14, 2026

(54) ULTRAVIOLET LIGHT-BLOCKING COMPOSITION COMPRISING CENTIPEDE GRASS EXTRACT AND COSMETIC COMPOSITION COMPRISING SAME

(71) Applicant: KOREA ATOMIC ENERGY RESEARCH INSTITUTE, Daejeon (KR)

(72) Inventors: Byung-Yeoup Chung, Jeollabuk-do (KR); Hyoung-Woo Bai, Jeongeup-si (KR); Seong-Hee Kang, Jeonju-si (KR); Sung-Beom Lee, Gwangju (KR); Seung-Sik Lee, Jeongeup-si (KR); Tae-Hoon Kim, Gyeongsan-si (KR); Mi-Yeon Kim, Jeongeup-si (KR)

(73) Assignee: KOREA ATOMIC ENERGY RESEARCH INSTITUTE, Daejeon (KR)

( * ) Notice: Subject to any disclaimer, the term of this patent is extended or adjusted under 35 U.S.C. 154(b) by 349 days.

(21) Appl. No.: 18/270,763

(22) PCT Filed: Jan. 6, 2022

(86) PCT No.: PCT/KR2022/000215
§ 371 (c)(1),
(2) Date: Jul. 3, 2023

(87) PCT Pub. No.: WO2022/149870
PCT Pub. Date: Jul. 14, 2022

(65) Prior Publication Data
US 2024/0074965 A1 Mar. 7, 2024

(30) Foreign Application Priority Data
Jan. 7, 2021 (KR) ........................ 10-2021-0002118

(51) Int. Cl.
*A61K 8/9794* (2017.01)
*A61K 8/37* (2006.01)
(Continued)

(52) U.S. Cl.
CPC ............ *A61K 8/9794* (2017.08); *A61K 8/375* (2013.01); *A61K 8/498* (2013.01); *A61K 8/602* (2013.01); *A61Q 17/04* (2013.01)

(58) Field of Classification Search
CPC ...... A61K 8/9794; A61K 8/375; A61K 8/498; A61K 8/602; A61Q 17/04
See application file for complete search history.

(56) References Cited

U.S. PATENT DOCUMENTS

2011/0142897 A1    6/2011  Cotton et al.
2013/0243836 A1*   9/2013  Tanner ................. A61K 8/0254
                                                  424/59
(Continued)

FOREIGN PATENT DOCUMENTS

CN        102106642 A      6/2011
CN        104812399 A      7/2015
(Continued)

OTHER PUBLICATIONS

Communication dated Sep. 5, 2025 in Chinese Application No. 202280009172.8.
(Continued)

*Primary Examiner* — Jianfeng Song
(74) *Attorney, Agent, or Firm* — Sughrue Mion, PLLC

(57) ABSTRACT

The present disclosure relates to an ultraviolet light-blocking composition containing a centipede grass extract and a cosmetic composition and, more specifically, to an ultraviolet light-blocking composition comprising a centipede grass
(Continued)

(Eremochloa ophiuroides) leaf extract as an active ingredient; and a cosmetic composition containing the ultraviolet light-blocking composition.

3 Claims, 6 Drawing Sheets

(51) Int. Cl.
| | |
|---|---|
| *A61K 8/49* | (2006.01) |
| *A61K 8/60* | (2006.01) |
| *A61Q 17/04* | (2006.01) |

(56) References Cited

U.S. PATENT DOCUMENTS

| | | | |
|---|---|---|---|
| 2015/0265667 A1 | 9/2015 | Bai et al. | |
| 2019/0336560 A1* | 11/2019 | Chung | .......... A61K 36/889 |

FOREIGN PATENT DOCUMENTS

| | | | |
|---|---|---|---|
| CN | 105748349 A | | 7/2016 |
| CN | 109952111 A | | 6/2019 |
| JP | 8-151319 A | | 6/1996 |
| KR | 10-2011-0040363 A | | 4/2011 |
| KR | 10-2011-0040375 A | | 4/2011 |
| KR | 10-2011-0054747 A | | 5/2011 |
| KR | 20110054746 | * | 5/2011 |
| KR | 20110054747 | * | 5/2011 |
| KR | 10-2013-0087650 A | | 8/2013 |
| KR | 101350827 B1 | | 1/2014 |
| KR | 10-2016-0037407 A | | 4/2016 |
| KR | 10-2017-0033698 A | | 3/2017 |
| KR | 10-2092595 B1 | | 3/2020 |
| KR | 10-2020-0102384 A | | 8/2020 |

OTHER PUBLICATIONS

International Search Report for PCT/KR2022/000215 dated Apr. 12, 2022.

Written Opinion for PCT/KR2022/000215 dated Apr. 12, 2022.

Seong Hee Kang, et al.,. "Radioprotective effects of centipedegrass extract on NIH-3T3 fibroblasts via anti-oxidative activity", Experimental and Therapeutic Medicine, vol. 21, No. 419, 2021, pp. 1-10.

Extended European Search Report issued Jul. 12, 2024 in Application No. 22736847.9.

* cited by examiner

ULTRAVIOLET LIGHT-BLOCKING COMPOSITION COMPRISING CENTIPEDE GRASS EXTRACT AND COSMETIC COMPOSITION COMPRISING SAME

CROSS REFERENCE TO RELATED APPLICATIONS

This application is a National Stage of International Application No. PCT/KR2022/000215 filed Jan. 6, 2022, claiming priority based on Korean Patent Application No. 10-2021-0002118 filed Jan. 7, 2021, the entire disclosures of which are incorporated herein by reference.

TECHNICAL FIELD

The present disclosure relates to an ultraviolet light-blocking composition comprising a centipede grass extract and a cosmetic composition comprising the same, and more particularly, to a composition capable of effectively blocking ultraviolet rays by using a centipede grass (Eremochloa ophiuroides) extract whose UV blocking effect is not known at all.

BACKGROUND ART

Due to the recent increase in the issue of chemical ingredients, consumers who check all ingredients when purchasing cosmetics or prefer natural ingredients with low irritation are increasing. Accordingly, in the cosmetics market, cosmetics made of natural ingredients excluding chemical substances are becoming the mainstream, and cosmetics using these natural ingredients are being released. In particular, since it has been reported that most of the ultraviolet light-blocking materials used in sunscreen are made of chemical substances, and thus, various serious side effects such as skin rash occur, replacement with natural materials is the most urgent. In addition, as it is known that the destruction of an ozone layer due to environmental pollution, increased outdoor activity, and excessive exposure may cause skin aging such as wrinkles, pigmentation, and loss of elasticity, sunburn, erythema, blackening, skin cancer, and the like, the importance of blocking UV is increasing.

In general, an ultraviolet ray (UV) includes UVC (200 to 290 nm) that is completely absorbed by ozone in the stratosphere, UVB (290 to 320 nm), most of which is absorbed by the ozone layer, but some of which reaches the Earth's surface, and UVA (320 to 400 nm) that is not absorbed by the ozone layer and has a longer wavelength than other types of UV. It is known that the UVA may cause long-term skin damage due to skin aging by acting on a skin immune system while making the skin red. The UVB may burn the skin and penetrate into skin tissue to cause burns in a short time, and is known to be a major cause of skin cancer. In addition, it has been known that the UVC has the shortest wavelength and high energy among UV rays, causing genetic mutations and causing serious skin damage, but almost all of the UVC is blocked by the ozone layer and does not reach the earth's surface.

The sunscreen is a product applied to the skin to protect the skin from the harmful UV, and uses organic or inorganic ultraviolet light-blocking materials, which may absorb or scatter UV, to prevent the skin from being excessively exposed to UV. However, since the components of the existing organic ultraviolet light-blocking material themselves are composed of organic compounds, in the case of the sensitive skin, the existing organic ultraviolet light-blocking material may cause irritant dermatitis symptoms specific chemical due to ingredients. Meanwhile, the inorganic ultraviolet light-blocking materials are capable of blocking UV rays in a wide area, but the inorganic ultraviolet light-blocking materials are difficult to be dispersed and dissolved and cause a whitening phenomenon, so there is a problem in that the inorganic ultraviolet light-blocking materials have a limit in use in a large amount and a poor feeling of use. Meanwhile, Korean Patent Publication No. KR 10-2092595 discloses a cosmetic composition for UV screening containing a *chlorella* extract as an active ingredient, but discloses that an SPF blocking index of the *chlorella* extract was evaluated as about 15.3 and cell viability of a human keratinocyte cell line (HaCaT cells) is rapidly reduced at a concentration of 1 mg/mL or more.

Therefore, when natural materials exhibiting an excellent blocking effect against UVB, which has a shorter wavelength and higher energy than UVA to cause serious skin damage, among the ultraviolet rays reaching the Earth's surface, are found, the natural materials are expected to be usefully applied in related fields.

DISCLOSURE

Technical Problem

The present disclosure provides an ultraviolet light-blocking composition comprising a natural plant extract having an excellent ultraviolet light-blocking effect.

The present disclosure provides a cosmetic composition comprising the ultraviolet light-blocking composition of the present disclosure.

Technical Solution

In an aspect in the present disclosure, there is provided an ultraviolet light-blocking composition comprising a centipede grass (Eremochloa ophiuroides) leaf extract as an active ingredient.

In another aspect in the present disclosure, there is provided a cosmetic composition comprising the ultraviolet light-blocking composition of the present disclosure.

Advantageous Effects

According to the present disclosure, since it is possible to effectively block UVB having a wavelength range of 280 to 320 nm using a centipede grass extract which is a non-toxic natural product compared to synthetic UV sunscreen components for which various side effects have been reported, the centipede grass extract of the present disclosure may be used as a new sunscreen, usefully used as an ultraviolet light-blocking composition composing the centipede grass extract as an active ingredient, and expected to be able to replace conventional synthetic ultraviolet light-blocking ingredients in external cosmetic compositions for various uses.

3

Figure 4:
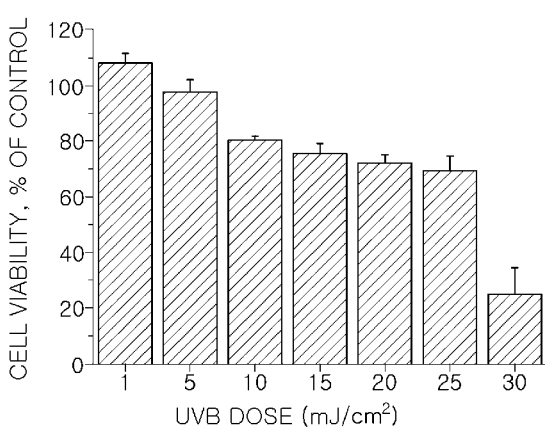

FIG. 4 is a diagram illustrating a change in cell viability of fibroblast after UVB irradiation.

Figure 5A:
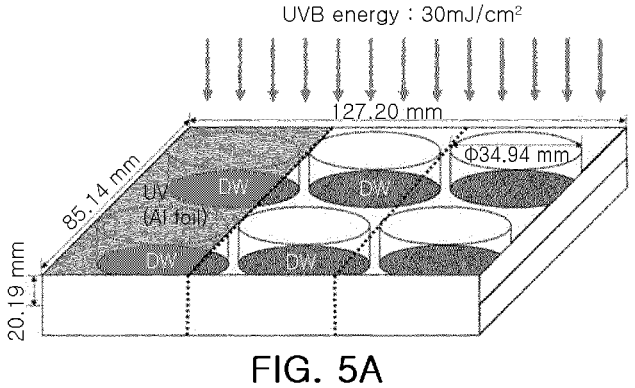
Figure 5B:
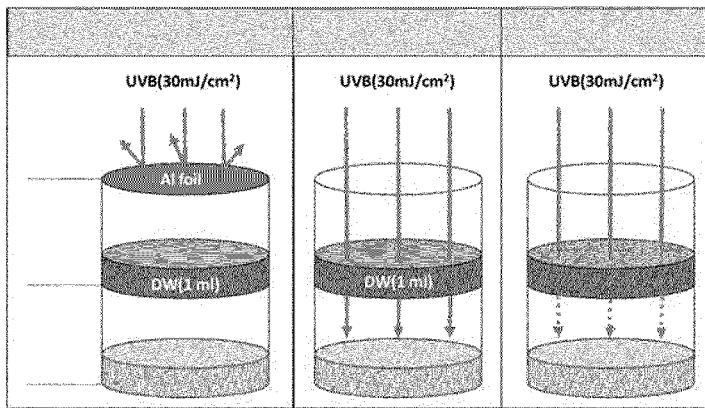

FIG. 5A-FIG. 5B are schematic diagrams of an in vitro experimental device for measuring a UVB protection effect of the centipede grass hot water extract, in which FIG. 5A is a perspective view of the device, and FIG. 5B is a cross-sectional view of the device.

Figure 6:
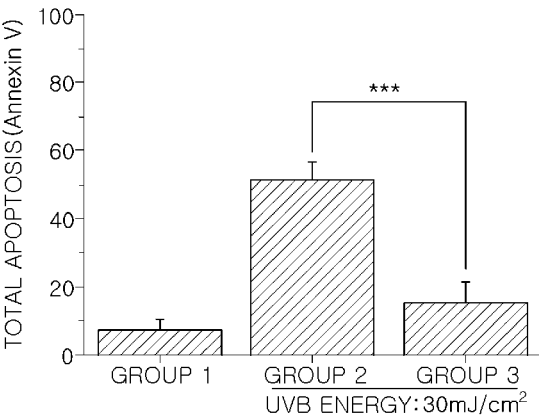

FIG. 6 is a diagram illustrating a UVB protection effect of the centipede grass hot water extract (p<0.001).

BEST MODE

Hereinafter, exemplary embodiments in the present disclosure will be described with reference to the accompanying drawings. However, exemplary embodiments in the present disclosure may be modified in several other forms, and the scope of the present disclosure is not limited to exemplary embodiments to be described below.

According to the present disclosure, there is provided an ultraviolet light-blocking composition comprising a centipede grass (Eremochloa ophiuroides) leaf extract as an active ingredient. The centipede grass is a late-growing, warm-season turfgrass, and is a perennial turf that forms a turf and grows prostrate. The centipede grass belongs to the Poaceae family, and its scientific name is Eremochloa ophiuroides (Munro) Hack. The centipede grass is mainly distributed in China, East Asia, Indochina, Northeastern United States, Mesoamerica, and the Caribbean regions, and adapts well to a wide variety of soil conditions, but is particularly well tolerated in moist, acidic soils, and sandy soils with low fertility. The present disclosure uses an aerial part of the Centipede grass, i.e., preferably leaves.

The centipede grass extract acquired by the present disclosure contains at least one of chlorogenic acid, orientin, isoorientin, rhamnosylisoorientin, derhamnosylmaysin, maysin, luteolin, and eremonetin, and preferably contains all of them.

The centipede grass leaf extract of the present disclosure is extracted by water, $C_1$ to $C_4$ lower alcohol, or a mixed solvent thereof, and the lower alcohol may be, for example, ethanol, methanol, etc., but is not limited thereto, and includes polyhydric alcohol such as 1,3-butylene glycol. Preferably, the centipede grass leaf extract of the present disclosure is a hot water extract using water as a solvent.

More detail, as an extraction method used to acquire the extract of the present disclosure, immersion extraction, shaking extraction, hot water extraction, reflux extraction, or the like may be used, but the extraction method is not limited thereto. For example, the centipede grass leaf extract may be extracted by adding 1 to 50 L of extraction solvent, and preferably 4 to 30 L of extraction solvent based on 1 kg of centipede grass leaves, but is not limited thereto. An extraction temperature is preferably 4 to 150° C., for example, 10 to 120° C., 25 to 100° C., or 50 to 120° C., but is not limited thereto, and an extraction time is preferably 2 to 5 days, but is not limited thereto. In addition, the number of times of extraction is preferably one to three times, but is not limited thereto. For example, the hot water extract may be acquired by being immersed at a temperature of 50° C. to 120° C., and preferably 50° C. or higher to less than 100° C. for 1 hour to 24 hours and extracted.

Meanwhile, in the present disclosure, the centipede grass leaf extract may be extracted in a liquid phase and used by itself, but is not limited thereto, and the extract may be used after being filtered one or more times, and the extract may be used after being concentrated or dried. For example, the filtration may use a Whatman filter paper of 0.2 to 8 μm, for example, a syringe filter having a pore size of 0.2 to 0.5 μm, or a combination thereof. In addition, for example, the concentration may be concentrated under reduced pressure, but is not limited thereto, and the drying may be performed by reduced pressure drying, vacuum drying, boiling drying, spray drying, freeze drying, or the like, but is not limited thereto.

Therefore, in the present disclosure, the "containing as an active ingredient" includes all cases in which the extract itself, its concentrate, its dried product, etc., are included as an active ingredient.

The ultraviolet light-blocking composition acquired by the present disclosure may be for blocking ultraviolet A (UVA) and ultraviolet B (UVB), for example, for blocking UVB, and particularly, exhibits excellent blocking effect against UVB.

According to another aspect of the present disclosure, there is provided a cosmetic composition comprising the ultraviolet light-blocking composition of the present disclosure.

The cosmetic composition of the present disclosure is not limited to the cosmetic composition for blocking ultraviolet rays, and the ultraviolet light-blocking composition of the present disclosure may be used in cosmetic compositions for various purposes as an additive.

In this case, the cosmetic composition may contain the ultraviolet light-blocking composition in an amount of 0.1% to 2% by weight, for example, 0.5% to 1.5% by weight, and preferably 1% by weight based on a total weight of the cosmetic composition. However, the contents of the centipede grass extract in the cosmetic composition may vary depending on the concentration of the centipede grass (Eremochloa ophiuroides) extract included in the ultraviolet light-blocking composition of the present disclosure, and the form of liquid or dry powder, and is not limited to the above range.

The cosmetic composition may be provided, for example, in the form of solution, gel, solid or pasty anhydrous product, emulsion obtained by dispersing an oil phase in an aqueous phase, suspension, microemulsion, microcapsule, microgranules, or an ionic (liposome), non-ionic vesicular dispersant, or in the form of cream, skin, lotion, powder, ointment, spray, or conceal stick. In addition, the cosmetic composition may be prepared in the form of a foam or in the form of an aerosol composition further containing a compressed propellant.

In addition, the cosmetic composition may include, in addition to the centipede grass extract of the present disclosure, a fatty substance, an organic solvent, a solvent, a thickening and gelling agent, a softener, a antioxidant, a suspending agent, a stabilizer, a foaming agent, an air freshener, a surfactant, water, an ionic or nonionic emulsifier, a filler, a metal ion sequester and chelating agent, a preservative, vitamin, a blocking agent, a wetting agent, essential oil, dye, pigment, a hydrophilic or lipophilic active agent, lipid vesicle, or adjuvants commonly used in cosmetics, such as any other ingredient commonly used in cosmetics.

Hereinafter, the present disclosure will be described in more detail through specific examples. The following examples are merely illustrative to help the understanding of the present disclosure, and the scope of the present disclosure is not limited thereto.

Mode for Disclosure

Example

1. Preparation of Centipede Grass Extract
(1) Preparation of Centipede Grass Ethanol Extract Centipede e grass seeds were grown in the packaging of Advanced Radiation Technology Institute of the Korea Atomic Energy Research Institute located in Jeongeup to collect a centipede grass leaf samples. The collected leaf samples were naturally dried at 20 to 24° C. for one week and then dried at 105° C. for 24 hours to measure the moisture contents in the samples. The water contents (WC) measurement formula of the collected leaf sample are as shown in [Equation 1] below.

$$WC(\%) = \frac{SW_1(g) - SW_2(g)}{SW_1(g)} \times 100(\%) \qquad \text{[Equation 1]}$$

WC (Water Contents, %)=Moisture contents
SW$_1$ (Sample Weight, g)=Weight of centipede grass leaf sample before natural drying.
SW$_2$ (Dried Sample Weight, g)=Weight of centipede grass leaf sample measured after natural drying at 20 to 24° C. for one week and drying at 105° C. for 24 hours The water contents in the centipede grass leaf sample measured through the above [Equation 1] were measured to be 8.93±0.48%. The extract obtained by adding 2 L of 80% ethanol (EtOH) to 250 g of dried centipede grass leaves and immersing the leaves at room temperature for 3 days was filtered twice using Whatman filter papers (No. 2, 110 mm). Thereafter, the centipede grass ethanol extract was obtained by being filtered once using a syringe filter of 0.45 μm.

(2) Preparation of Centipede Grass Methanol Extract

Centipede grass seeds were grown in the packaging of Advanced Radiation Technology Institute of the Korea Atomic Energy Research Institute to collect centipede grass leaf samples. The extract obtained by adding 2 L of 80% methanol (MeOH) to 250 g of centipede grass leaves dried by the same process as the above 1. (1) and immersing the leaves at room temperature for 3 days was filtered twice using Whatman filter papers (No. 2, 110 mm). Thereafter, the centipede grass methanol extract was obtained by being filtered once using a syringe filter of 0.45 μm.

(3) Preparation of Centipede Grass Hot Water Extract

Centipede grass seeds were grown in the packaging of Advanced Radiation Technology Institute of the Korea Atomic Energy Research Institute to collect centipede grass leaf samples. The extract obtained by adding 5 L of water to 250 g of centipede grass leaves dried by the same process as the above 1. (1) and immersing the leaves at 90° C. for 6 hours was filtered twice using Whatman filter papers (No. 2, 110 mm). Thereafter, the centipede grass hot water extract was obtained by being filtered once using a syringe filter of 0.45 μm.

(4) Preparation of Centipede Grass Water Extract

Centipede grass seeds were grown in the packaging of Advanced Radiation Technology Institute of the Korea Atomic Energy Research Institute to collect centipede grass leaf samples. The extract obtained by adding 2 L of water to 250 g of centipede grass leaves dried by the same process as the above 1. (1) and immersing the leaves at room temperature for 3 days was filtered twice using Whatman filter papers (No. 2, 110 mm). Thereafter, the centipede grass water extract was obtained by being filtered once using a syringe filter of 0.45 μm.

(5) Preparation of Centipede Grass 1,3-Butylene Glycol Extract

Centipede grass seeds were grown in the packaging of Advanced Radiation Technology Institute of the Korea Atomic Energy Research Institute to collect centipede grass leaf samples. The extract obtained by adding 2 L of 70% 1,3-butylene glycol to 250 g of centipede grass leaves dried by the same process as the above 1. (1) and immersing the leaves at room temperature for 24 hours was filtered twice using Whatman filter papers (No. 2, 110 mm). Thereafter, the centipede grass 1,3-butylene glycol extract was obtained by being filtered once using a syringe filter of 0.45 μm.

2. Check Density and Extraction Yield of Hot Water Extract
(1) Density Measurement of Centipede Grass Hot Water Extract In order to measure the density (ρ) of the centipede grass hot water extract of the present disclosure, the experiment was conducted as follows.

①  Five Erlenmeyer flasks (glassware; 300 mL) having the same volume were subjected to ultrasonic cleaning, and then, completely dried at 105° C. for 24 hours.

②  After the five Erlenmeyer flasks (glassware; 300 mL) of the above 1 were sufficiently cooled, each of the Erlenmeyer flasks was weighed.

③  100 mL of centipede grass hot water extract obtained in the above 1. (3) was put into the Erlenmeyer flask of the above ②, and then, completely dried at 105° C. for 24 hours.

④  The Erlenmeyer flask completely dried in ③ above was weighed.

⑥  The density was calculated by substituting the weight measured through the above process into the following [Equation 2].

$$\rho(g/L) = \frac{FW_2(g) - FW_2(g)}{SV(L)} \qquad \text{[Equation 2]}$$

ρ (Density, g/L)=Density of centipede grass hot water extract.
FW$_1$ (Flask Weight, g)=Weight of a completely dried Erlenmeyer flask
FW$_2$ (Flask & Sample Weight, g)=Weight of a completely dried Erlenmeyer flask containing centipede grass hot water extract dried for 24 hours at 105°
SV (Sample Volume, L)=Volume of centipede grass hot water extraction (100 mL)

As a result, the density of the centipede grass hot water extract calculated through the above [Equation 2] was measured to be 6.4±0.1 mg/mL.

(2) Measurement of Extraction Yield of Centipede Grass Hot Water Extract

The extraction yield of the hot water extract of the centipede grass of the present disclosure was calculated using the following [Equation 3].

$$EY(\%) = \frac{ESW_2(g)}{ESW_1(g)} \times 100(\%) \qquad \text{[Equation 3]}$$

7

EY (Extraction Yield, %)=Extraction yield $ESW_1$ (Non-extracted Sample Weight, g)=Weight of dried centipede grass leaf sample used for hot water extraction.

$ESW_2$ (Extracted Sample Weight, g)=Weight of centipede grass hot water extract measured after hot water extraction and complete drying at 105° C. for 24 hours As a result, the extraction yield of the centipede grass hot water extract calculated through the above [Equation 3] was measured to be 9.04%/mL.

3. In Vitro SPF Measurement of Centipede Grass Extract

In order to confirm the UV blocking ability of the centipede grass extract against UVB having a wavelength of 290 to 320 nm, the sun protection factor (SPF) was measured.

The SPF measurement in this experiment referenced the method of RM Sayre et al. (RM Sayre, et al. A comparison of in vivo and in vitro testing of sunscreening formulas. Photochemistry and photobiology, 1979, 29 (3), pp. 559-566). The in vitro SPF measurement equation used in the present disclosure is as shown in [Equation 4] below.

$$SPF = CF \times \sum_{290}^{320} EE(\lambda) \times I(\lambda) \times \text{Abs}(\lambda) \qquad \text{[Equation 4]}$$

CF=Correction Factor=10

EE($\lambda$)=Erythema effect of solar radiation at each wavelength $\lambda$

I($\lambda$)=Solar intensity at wavelength $\lambda$

Abs($\lambda$)=Absorbance of sample measured at each wavelength $\lambda$

Here, the values in Table 1 below were applied to the EE X I value.

TABLE 1

| Wavelength (nm) | EE X I (normalized) |
|---|---|
| 290 | 0.0150 |
| 295 | 0.0817 |
| 300 | 0.2874 |
| 305 | 0.3278 |
| 310 | 0.1864 |
| 315 | 0.0839 |
| 320 | 0.0180 |
| Total | 1.0000 |

8

SPF measurement of each of the centipede grass extracts obtained in the above 1. was performed as follows.

① Each of the centipede grass extracts obtained in the above 1. (1) to 1. (5) was diluted with each solvent so that the centipede grass extracts were finally 10 mg/mL, 5 mg/mL, 2.5 mg/mL, 1 mg/mL, 0.5 mg/mL, and 0.1 mg/mL.

② The solution (100 UL) of the above 1) was put in a 96-well black plate, and the absorbance of the extract was measured using a spectrophotometer (Tecan, Mannedorf, Switzerland) at intervals of 5 nm from 230 nm to 400 nm. Each solvent (80% ethanol, 80% methanol, water, and 70% 1,3-butylene glycol) used for extraction in the above 1. (1) to 1. (5) was used as a standard (blank) (corresponds to 'each solvent' in Table 2 below).

③ The in vitro SPF values calculated by substituting the absorbance measured in the above ② into the above [Equation 4] and Table 1 were shown in Table 2 below.

TABLE 2

In vitro SPF measurement values of each centipede grass extract

| Extraction Solvent | Concentration (mg/mL) | | | | | | Each solvent | Blank |
|---|---|---|---|---|---|---|---|---|
| | 10 | 5 | 2.5 | 1 | 0.5 | 0.1 | | |
| Ethanol | 19.86 | 12.71 | 5.58 | 3.18 | 1.44 | 1.30 | 1.73 | 1.36 |
| Methanol | 17.91 | 11.43 | 4.03 | 2.98 | 1.31 | 1.23 | 1.16 | 1.36 |
| Hot water | 38.05 | 38.28 | 37.49 | 22.04 | 11.75 | 1.76 | 1.27 | 1.36 |
| Water | 21.63 | 15.36 | 9.81 | 4.98 | 1.98 | 1.36 | 1.20 | 1.36 |
| 1,3-butylene glycol | 14.20 | 8.23 | 4.11 | 2.86 | 1.43 | 1.31 | 1.27 | 1.36 |

In Table 2, the blank means an empty well. It was confirmed based on the SPF measurement results of the centipede grass extracts obtained in the above 1. that the centipede grass ethanol extract (10 mg/mL) obtained in the above 1. (1) blocks about 94.9% of UVB, the centipede grass methanol extract (10 mg/mL) obtained in the above 1. (2) blocks about 94.4% of UVB, the centipede grass hot water extract (10 mg/mL) obtained in the above 1. (3) blocks about 97.3% of UVB, the centipede grass water extract (10 mg/mL) obtained in the above 1. (4) blocks about 95.4% of UVB, and the centipede grass 1,3-butylene glycol extract (10 mg/mL) obtained in the above 1. (5) blocks about 92.9% of UVB.

Figure 1:
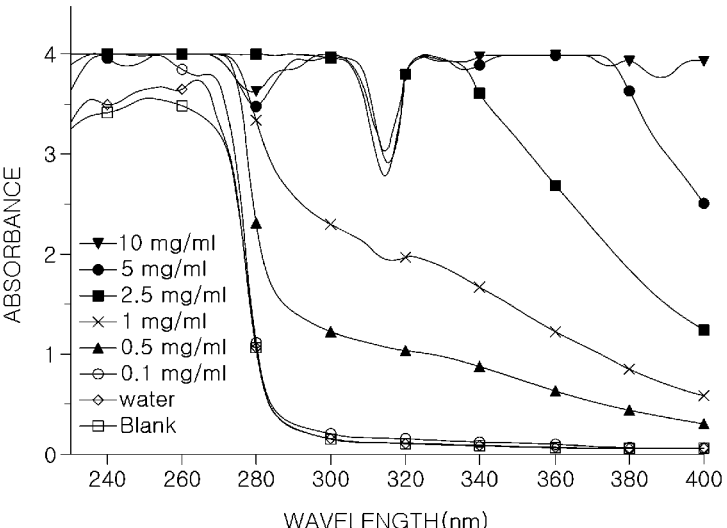
FIG. 1 is a diagram illustrating an absorbance measurement result of a centipede grass hot water extract.

As such, it was confirmed that the centipede grass extract showed all excellent UVB blocking effects in various extraction solvents, and in particular, the UVB blocking effect of the centipede grass hot water extract obtained in the above 1. (3) was superior to that of other solvents. FIG. 1 showed the UV wavelength band absorbance measurement results of the centipede grass hot water extract obtained in the above 1. (3).

4. Ingredient Analysis of Centipede Grass Hot Water Extract

The HPLC analysis was performed to analyze the ingredients of the centipede grass hot water extract of the present disclosure. Specifically, 20 µL of the sample solution (centipede grass hot water extract obtained in the above 1. (3)) was injected into an Agilent Technologies 1200 series HPLC, and a mobile phase composed of a 1% formic acid aqueous solution (solution (A) and a 100% methanol (solution B) was used. Fraction components were eluted using the mobile phase in a combined step and a linear gradient of 100:0 (solution A:B) to 50:50 for 30 minutes, followed by a linear gradient of 50:50 to 0:100 for 60 minutes. A flow rate was 0.5 µL/min and the eluted compound was detected at a wavelength of 360 nm.

Figure 2:
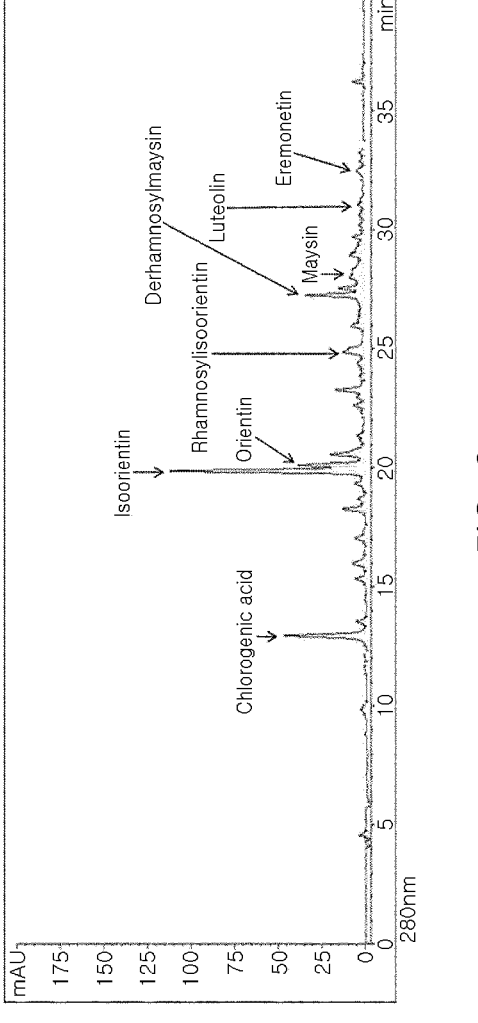
FIG. 2 is a diagram illustrating an HPLC analysis result of the centipede grass hot water extract.

As a result, as can be seen in FIG. 2, eight single substances of chlorogenic acid, orientin, isoorientin, rhamnosylisoorientin, derhamnosylmaysin, maysin, luteolin, and eremonetin were confirmed in the centipede grass hot water extract obtained in the above 1. (3), and their contents were shown in Table 3 below.

TABLE 3

| Ingredient | Chlorogenic acid | Orientin | Isoorientin | Rhamnosylisoorientin | Derhamnosylmaysin | Maysin | Luteolin | Eremonetin |
|---|---|---|---|---|---|---|---|---|
| μg/g | 67.6 | 7.3 | 54.0 | 137.5 | 157.4 | 107.2 | 34.1 | 85.6 |

*The above Table 3 showed the contents of each ingredient per 1 mg of the extract in μg.

5. Measurement of Total Phenolic Content and Total Flavonoids Content in Centipede Grass Hot Water Extract (1) Measurement of Total Phenolic Content in Centipede Grass Hot Water Extract Phenolic compounds collectively refer to flavonoids, anthocyanins, tannins, catechins, isoflavones, lignans, resveratrols, and the like, and are widely distributed in the plant kingdom. A large number of hydroxyl groups (—OH) present in phenols are known to have excellent antioxidant and anti-inflammatory effects because they have the property of easily bonding to various compounds. Therefore, in order to examine the antioxidant efficacy of the centipede grass hot water extract obtained in the above 1. (3), the total phenolic content in the centipede grass hot water extract was measured. The total phenolic content was measured using the principle that a Folin-reagent is reduced by a phenolic compound to develop a molybdenum blue color.

Specifically, the phenolic content of the centipede grass hot water extract was calculated as an equivalent weight based on a standard calibration curve obtained by preparing the standard material at a concentration of 0 to 100 μg/mL using gallic acid and then analyzing in the same way as the centipede grass hot water extract. The centipede grass hot water extract was mixed with a Folin-Ciocalteau's phenol reagent and reacted at room temperature for 1 hour while blocking light. Thereafter, after dispensing the centipede grass hot water extract into each 96-well plate by 200 μL, the absorbance was measured at 765 nm using a spectrophotometer (Tecan, Mannedorf, Switzerland). The total phenolic content eluted from 1 g of dried centipede grass hot water extract was measured based on the gallic acid.

Figure 3A:
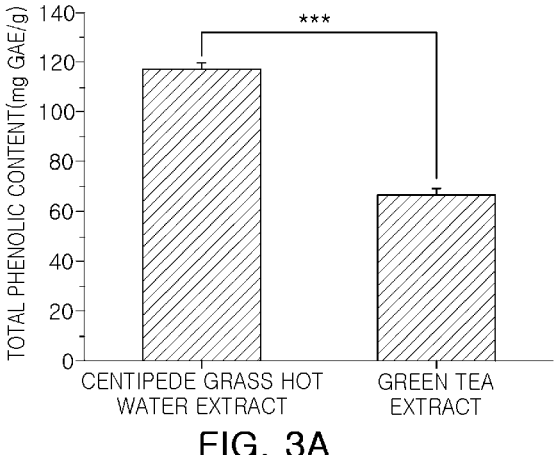
FIG. 3A-FIG. 3B are diagrams illustrating the total phenolic content (FIG. 3A) and total flavonoids content (FIG. 3B) in the centipede grass hot water extract compared to a green tea extract ($p<0.001$).

As a result, as can be seen in FIG. 3A, the total phenolic content in the centipede grass hot water extract obtained in the above 1. (3) was 117.0±2.3 mg GAE/g, which was measured to be significantly higher than the green tea extract (66.7±1.3 mg GAE/g) used as a control group.

(2) Measurement of Total Flavonoids Content in Centipede Grass Hot Water Extract The flavonoids are an ingredient belonging to a phenol class, and are contained in almost all parts of plants, such as leaves, flowers, fruits, stems, and roots of plants, like polyphenols with C6-C3-C6 as a basic skeleton of the flavonoids. Like the phenols, the flavonoids are known to have anti-inflammatory and antioxidant effects. Therefore, in order to examine the antioxidant efficacy of the centipede grass hot water extract obtained in the above 1. (3), the total flavonoids content in the centipede grass hot water extract was measured.

Specifically, 10% $Al(NO_3)_3$ and 1 M $KCH_3CO_2$ were each added to 500 μL of mixture, which was prepared by mixing the centipede grass hot water extract and methanol at a ratio of 1:9, by 100 μL. 4.3 mL of methanol was added to the mixture and then reacted at room temperature for 40 minutes, and then, the absorbance was measured at 415 nm using the spectrophotometer. The total flavonoids content in the centipede grass hot water extract was checked using quercetin by comparing with a standard curve drawn in the same method as the above procedure.

Figure 3B:
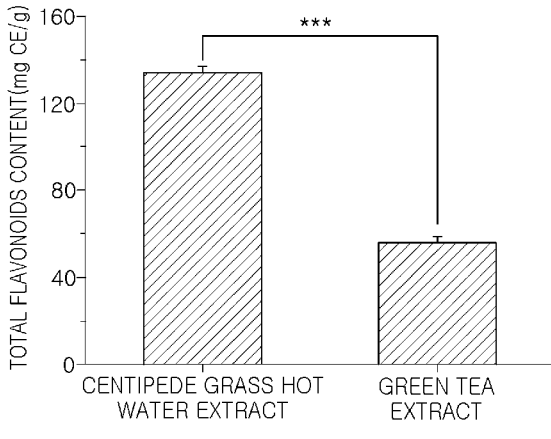

As a result, as can be seen in FIG. 3B, the total flavonoids content in the centipede grass hot water extract obtained in the above 1. (3) was 133.8±2.1 mg CE/g, which was measured to be significantly higher than the green tea extract (56.2±0.5 mg GAE/g) used as a control group.

6. Analysis of UVB Protection Effect of Centipede Grass Hot Water Extract on Fibroblast In order to confirm whether the centipede grass hot water extract of the present disclosure obtained in the above 1. (3) has a protective effect against UVB in fibroblast (Human, fibroblast), the following experiment was performed.

(1) Fibroblast Cell Line Culture

In order to confirm the UVB protection effect of the centipede grass hot water extract of the present disclosure, the fibroblast was purchased from the Korean Cell Line Bank (KCLB). The fibroblasts (CCD-986SK, Human) were cultured in IMDM (Isocove's modified Dulbecco's medium) containing 10% FBS (fetal bovine serum) together with 100 U/mL penicillin and 100 μg/mL streptomysin, and maintained at 37° C. and 5% $CO_2$ culture environment.

(2) Evaluation of UVB Cytotoxicity

To evaluate the UVB protective effect of the centipede grass hot water extract, the cytotoxicity of the UVB in the fibroblast was evaluated.

Specifically, the fibroblast ($1 \times 10^4$ cells/well) cultured in the above 6. (1) was dispensed into a 96-well plate and cultured for 6 hours in the culture medium containing 10% FBS. The cells were treated with FBS-free culture medium and then cultured overnight. Thereafter, the UVB having various intensities (1, 5, 10, 15, 20, 25, 30 mJ/cm²) was irradiated and further cultured for 24 hours. Thereafter, after removing all the culture medium, the cells were washed once with phosphate buffer saline (PBS), and cultured at 37° C. for 3 hours in a culture medium including 100 μg/mL of MTT [3-(4,5-dimethylthiazol-2-yl)-2,5-diphenyltetrazolium bromide]. Thereafter, the cells were washed once with PBS and dissolved with 100 μL of dimethyl sulfoxide (DMSO). Intracellular purple formazan was quantified at 540 nm absorbance using an infinite M200 (TECAN, Mannedorf, Switzerland).

As a result, as illustrated in FIG. 4, the fibroblast activity irradiated with UBV of 1 and 5 mJ/cm² was 107.6±3.8 and 97.6±4.6%, which was not significantly different from that of a control group. On the other hand, the fibroblast activity irradiated with 10, 15, 20, 25 and 30 mJ/cm² was 80.1±1.6, 75.2±3.8, 72.2±2.9, 69.4±5.2 and 25.0±9.5%, which was significantly decreased in proportion to the irradiation intensity.

(3) In vitro SPF Measurement for Change in Fibroblast Culture Condition

In order to exclude the fact that the UBV protective effect of the centipede grass hot water extract of the present disclosure depends on the culture conditions of the fibroblast (type and dose of culture medium), the SPF values for the changes in the type and dose of the cell culture medium were measured/compared.

Specifically, the SPF measurement for the change in the type and dose of the cell culture medium was performed as follows.

11 12

① The centipede grass hot water extract obtained in the above 1. (3) was put into each 96-well black plate by 20, 40, 60, 80, 100, 120, 140, 160, 180, and 200 μL, and the absorbance of the extract was measured using the spectrophotometer at intervals of 5 nm from 230 nm to 400 nm.

② The PBS was put into each 96-well black plate by 20, 40, 60, 80, 100, 120, 140, 160, 180, and 200 μL, and the absorbance of the extract was measured using the spectrophotometer at intervals of 5 nm from 230 nm to 400 nm.

③ Isocove's modified Dulbecco's medium (IMDM) containing 10% fetal bovine serum (FBS) was put into each 96-well black plate by 20, 40, 60, 80, 100, 120, 140, 160, 180, and 200 μL together with 100 U/mL penicillin and 100 μg/mL streptomysin prepared in the above 6. (1), and the absorbance of the extract was measured using the spectrophotometer at intervals of 5 nm from 230 nm to 400 nm.

④ The in vitro SPF values calculated by substituting the absorbance measured in the above ① to ③ into the above [Equation 4] and Table 1 were shown in Table 4 below.

① Control group (group 1)
Upper layer 6-well plate (plate 1): Containing 1 mL of DW
Lower layer 6-well plate (plate 2): Fibroblast is placed in 1 mL of PBS
30 mJ/cm² UVB irradiation: State in which UVB is shielded by being wrapped with upper and lower layer 6-well plate foils ② UVB irradiation experimental group (Group 2)
Upper layer 6-well plate (plate 1): Containing 1 mL of DW
Lower layer 6-well plate (plate 2): Fibroblast is placed in 1 mL of PBS
30 mJ/cm² UVB irradiation ③ UVB irradiation and centipede grass hot water extract experimental group (group 3)
Upper layer 6-well plate (plate 1): Containing 1 mL of centipede grass hot water extract (1 mg/mL)
Lower layer 6-well plate (plate 2): Fibroblast is placed in 1 mL of PBS
30 mJ/cm² UVB irradiation After the cells of each experimental group were irradiated with UVB at an intensity of 30 mJ/cm², all the culture medium was removed, treated with the culture medium

TABLE 4

In vitro SPF measurement values for changes in type and dose of cell culture medium

| Type of Culture Medium | Dose (μL) | | | | | | | | | |
|---|---|---|---|---|---|---|---|---|---|---|
| | 20 | 40 | 60 | 80 | 100 | 120 | 140 | 160 | 180 | 200 |
| Hot Water Extract | 2.3 | 24.1 | 36.4 | 37.2 | 36.6 | 36.9 | 36.8 | 36.2 | 35.8 | 36.6 |
| PBS | 1.3 | 1.3 | 1.3 | 1.3 | 1.4 | 1.3 | 1.4 | 1.4 | 1.4 | 1.4 |
| IMDM | 1.3 | 1.4 | 1.6 | 1.8 | 2.0 | 2.1 | 2.3 | 2.5 | 2.6 | 2.8 |

As a result, as illustrated in Table 4, the changes in the SPF values for the change in dose of the centipede grass hot water extract and PBS obtained in the above 1. (3) were not observed. On the other hand, the SPF value of IMDM increased from 1.3 to 2.8 as the dose increased. The UBV blocking efficiency of the IMDM increased from 23.1% to 64.3% in proportion to the dose. Therefore, it was confirmed that the IMDM itself exhibits the UVB blocking effect.

(4) Analysis of UVB Protection Effect in Fibroblast

In order to determine whether the centipede grass hot water extract obtained in the above 1. (3) of the present disclosure exhibits the protective effect on the fibroblast irradiated with the UVB, an apoptosis rate was measured by Annexin V analysis.

FIG. 5A and FIG. 5B are schematic diagrams of a UVB irradiation experiment summarizing the experimental process, in which FIG. 5A is a perspective view, and FIG. 5B is a cross-sectional view. Specifically, the fibroblast ($1\times10^6$ cells/well) cultured in the above 6.(1) was dispensed into a 6-well plate, and cultured overnight at 37° C. and 5% $CO_2$ in a culture medium containing 10% FBS. Thereafter, after removing all the culture medium, the fibroblast was washed once with the phosphate buffer saline (PBS), and another 6-well plate (plate 1) containing 1 mL of DW or the centipede grass extract of the present disclosure was superimposed on a 6-well plate (plate 2) in which the fibroblasts were cultured and placed as in FIG. 5B. The fibroblast cultured in the schematic diagram of the above experiment was classified into three groups as follows.

without the FBS, and cultured for 24 hours under 37° C. and 5% $CO_2$ conditions. Thereafter, after removing all the culture medium, the cells were washed once with the PBS, treated with 500 μL of trypsin in each well, and centrifuged at 3000 rpm for 3 minutes to obtain all cells (pellets). The fibroblast obtained through the above process was dyed using the Annexin V/PI assay kit (Muse Annexin V and Dead Cell Assay kits, MCH100105; EMD millipore, Billerica, MA USA), and then the apoptotic cells were quantitatively analyzed using a Muse™ cell analyzer (Muse 1.1.2; EMD millipore, Billerica, MA USA).

As a result, as illustrated in FIG. 6, a total of 51.2±5.7% of apoptosis was induced in the fibroblast of group 2 irradiated with UVB with an intensity of 30 mJ/cm². On the other hand, in the fibroblast of group 3 in which the UVB was shielded by the centipede grass hot water extract (1 mg/mL) obtained in the above 1. (3), it was confirmed that the apoptosis was significantly reduced to 15.3±6.2%. Therefore, it was confirmed that the centipede grass hot water extract of the present disclosure increases the survival rate of the fibroblast by effectively blocking the irradiated UVB.

While exemplary embodiments have been shown and described above, it will be apparent to those skilled in the art that modifications and variations could be made without departing from the scope of the present disclosure as defined by the appended claims.

The invention claimed is:
1. A method of blocking ultraviolet light, comprising applying a composition comprising a centipede grass (Er- emochloa ophiuroides) leaf extract as an active ingredient to a subject's skin in need thereof, wherein the centipede grass leaf extract is a hot water extract, which contains chlorogenic acid, orientin, isoorientin, rhamnosylisoorientin, derhamnosylmaysin, maysin, Luteolin, and Eremonetin, wherein a concentration of the centipede grass (Eremochloa ophiuroides) leaf extract is 0.5 mg/ml or more, and wherein the hot water extraction is performed at a temperature of 50° C. to 100° C. for 1 hour to 24 hours.

2. The method according to claim 1, wherein the centipede grass leaf extract is extracted using 1 to 50 L of extraction solvent based on 1 kg of centipede grass leaves.

3. The method according to claim 1, wherein the ultraviolet light-blocking composition is for blocking ultraviolet A and ultraviolet B.

* * * * *